United States Patent [19]

Ratcliffe

[11] 4,212,807
[45] Jul. 15, 1980

[54] PROCESS FOR DEACYLATING N-ACYL-6-SUBSTITUTED-2-[2-AMINOETHYLTHIO]-1-CARBADETHIAPEN-2-EM-3-CARBOXYLIC ACIDS

[75] Inventor: Ronald W. Ratcliffe, Matawan, N.J.

[73] Assignee: Merck & Co., Inc., Rahway, N.J.

[21] Appl. No.: 932,738

[22] Filed: Aug. 10, 1978

[51] Int. Cl.$^2$ ............................................ C07D 487/04
[52] U.S. Cl. ............................... 260/326.31; 424/274
[58] Field of Search ................................... 260/326.31

[56] References Cited

U.S. PATENT DOCUMENTS 3,950,357  4/1976  Kahan et al. ...................... 260/326.31

OTHER PUBLICATIONS

Okamura et al., J. Antibiotics, vol. 31, No. 5, pp. 480–482 (1978).

*Primary Examiner*—Mary C. Lee
*Attorney, Agent, or Firm*—Hesna J. Pfeiffer; James A. Arno; Julian S. Levitt

[57] ABSTRACT

Disclosed is a process for chemically cleaving the acyl group from N-acyl-6-substituted-2-[2-aminoethylthio]-1-carbadethiapen-2-em-3-carboxylic acids which proceeds via an imino chloride intermediate. The acylated substrate and the deacylated product are antibiotics.

1 Claim, No Drawings

PROCESS FOR DEACYLATING N-ACYL-6-SUBSTITUTED-2-[2-AMINOETHYLTHIO]-1-CARBADETHIAPEN-2-EM-3-CARBOXYLIC ACIDS

BACKGROUND OF THE INVENTION

This invention relates to a chemical (i.e., non-enzymatic) process for deacylating N-acyl-6-substituted-2-[2-aminoethylthio]-1-carbadethiapen-2-em-3-carboxylic acids (I); such acylated species (I) and corresponding deacylated forms are antibiotics:

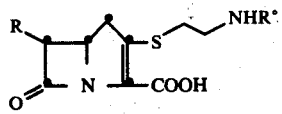

wherein R is, inter alia, hydroxyl substituted alkyl and R° is acyl. The most well known members of the series defined by structure I are the thienamycins wherein R is 1-hydroxyethyl and R° is acetyl; such products (1) are natural products of fermentation and are known:

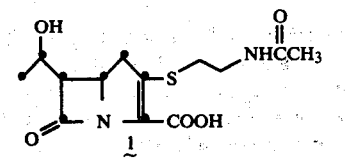

Species classified under sub-category (1) are alternatively known by the following nomenclature and are disclosed and claimed in the following co-pending, U.S. patent applications:

1. N-acyl thienamycin—U.S. patent application Ser. No. 827,503 (Aug. 25, 1977); and
2. 890A$_1$ and 890A$_3$—U.S. patent application Ser. No. 827,504 (Aug. 25, 1977) now U.S. Pat. No. 4,162,324, issued July 24, 1979 which applications are incorporated herein by reference.

A second sub-category (2) under generic structure I comprises sulfate esters of the carbinol which are natural products of fermentation and which bear the N-acetyl group:

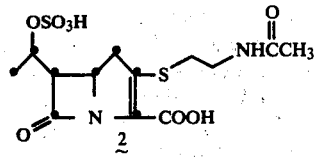

The species of sub-category 2 are known and are described and claimed in U.S. patent applications Ser. No. 860,662 (Dec. 15, 1977) now abandoned, in favor of U.S. Ser. No. 006,959, filed Jan. 25, 1979 and Ser. No. 891,799 (Mar. 30, 1978) which are incorporated herein by reference.

The third sub-category under generic structure I includes the 6-ethyl species (3):

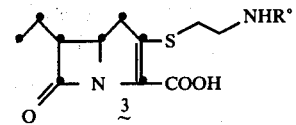

R° is acyl as defined above.

Species 3 is known (R°=acetyl) and available to the art; see the *Journal of Antibiotics,* Volume 31, No. 5, pages 480–482 (May 1978); such species and deacylated species are disclosed and claimed in co-pending, commonly assigned U.S. patent applications Ser. No. 861,230 (Dec. 16, 1977) now abandoned, in favor of U.S. Ser. No. 048,944, filed June 15, 1979 and 843,378 (Oct. 19, 1977) now abandoned in favor of its continuation-in-part U.S. Ser. No. 933,681 filed Aug. 17, 1978 which are incorporated herein by reference.

Finally, a fourth category (4) embraces the balance of products prepared by fermentation and those obtained by processes of total synthesis; category 4 is actually broader and more general than I. These compounds (4) are most conveniently represented by structure (I) above, but, in the most general case, are represented by structure 4:

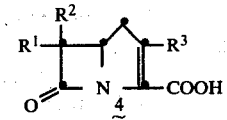

With respect to 4, R$^1$ and R$^2$ are, inter alia, independently selected from the group consisting of hydrogen, substituted and unsubstituted alkyl, aralkyl, aryl, alkenyl and the like and R$^3$ is a similarly broadly defined radical which is characterized for purposes of this process by having an amino group which is acylated. Such compounds 4 are disclosed and claimed in U.S. patent application Ser. No. 861,247 (Dec. 16, 1977); 843,378 (Oct. 19, 1977) now abandoned, in favor of U.S. Ser. No. 933,681, filed Aug. 17, 1978; 843,375 (Oct. 19, 1977); and 843,171 (Oct. 19, 1977); which are incorporated herein by reference.

The N-acyl species defined above I which includes the sub-categories 1, 2 and 3 and the generalized form 4 are all antibiotics. The species obtained by fermentation usually have acetyl as the acyl group; whereas those obtained by total synthesis are not limited to acetyl and may have any value for the acyl group. It is desirable, however, to have a process for obtaining the free amino compound since the deacylated species usually demonstrates enhanced antibiotic activity. Also, the deacylated antibiotic may also be regarded as an intermediate for subsequent derivatization of the amino group; such derivatization processes, however, are not embraced by the present invention.

DETAILED DESCRIPTION OF THE INVENTION

The preferred N-acyl substrates embrace the detailed categories 1, 2 and 3 above; preferred species falling under category 4 include those wherein R$^1$ and R$^2$ are independently selected from the group consisting of hydrogen, methyl, ethyl, benzyl, allyl, methoxyl, hydroxymethyl, 1-hydroxyethyl, 2-hydroxyethyl, 1-hydroxypropyl, 1-hydroxy-2-methylpropyl, 1-hydroxy- 3-phenyl-propyl, aminomethyl, mercaptomethyl, aminoethyl, mercaptoethyl, carboxymethyl and wherein $R^3$ is selected from amino N-acylated:

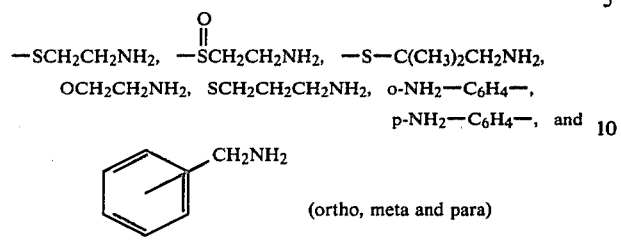

wherein the N-acyl group is selected from the group consisting of

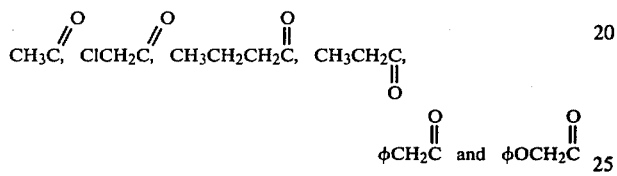

The process of the present invention may conveniently be described by the following diagram, which for purposes of general illustration carries the above-described species (4) through the process; the side chain at 2- is typical and for purposes of illustration. It is understood that all categories of substrate (I, 1, 2, 3 and 4) are similarly transformed (de-acylated) by the process:

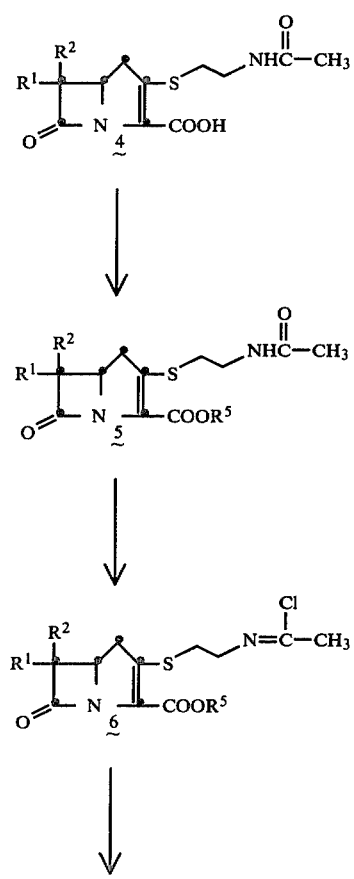

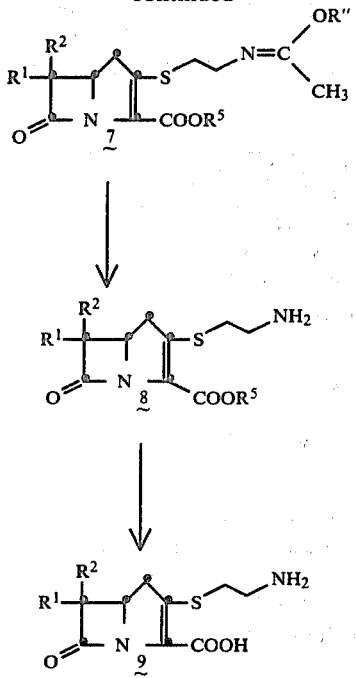

In words relative to the above diagram, the starting material, substrate 4, is subjected to the protecting transformation 4→5 to cover the carboxyl group with any well known, readily removable group. Suitable protecting groups $R^5$ include cleavable esters such as p-nitrobenzyl, mixed anhydride such as acylesters, such as

and organosilyl esters such as $Si(CH_3)_3$ and the like. It should be noted that when either $R^1$ or $R^2$ possesses a functional group which might interfere with the desired course of reaction it may also be protected in the same transformation 4→5. Typically, when $R^1$ or $R^2$ is hydroxylalkyl, protection is required. Protection by silylation is preferred for the protection of hydroxyl and carboxyl functions. Suitable reagents to accomplish such protective silylation include $(CH_3)_2SiCl_2$, $(CH_3)_3SiCl$, or the combination $(CH_3)_3SiCl$-$[CH_3]Si_2NH$ in the presence of a base such as N,N -dimethylaniline, N,N-diethylaniline, pyridine, quinoline or triethylamine. Suitable solvents include $CH_2Cl_2$, $CHCl_3$, tetrahydrofuran (THF), dioxane, benzene and the like at a temperature of from 0°–25° C. In general it will be appreciated that there is no criticality in the establishment of such protecting groups, their precise identity, or their ultimate removal for such technology is well within the routine of the art; see for example co-pending, U.S. patent application Ser. No. 861,246 filed Dec. 16, 1977 which is incorporated herein by reference to the extent that it describes relevant procedures for protecting carboxyl, hydroxyl and other groups. The chlorination reaction (5→6) of the amide side chain is conducted in the presence of a base such as pyridine, quinoline, N,N-dimethylaniline, N,N-diethylaniline, triethylamine, N-methylmorpholine or the like in the presence of a chlorinating agent such as $PCl_5$, SOCl₂, POCl₃, or the like in a solvent such as CCl₄, CH₂Cl₂, CHCl₃, benzene, dioxane or the like at a temperature of from −50° to 65° C.

The reaction 6→7 is typically conducted in a solvent such as CCl₄, CH₂Cl₂, CHCl₃, benzene, dioxane or the like in the presence of a 10-100 fold excess of an alcohol, R"OH, wherein R" is lower alkyl having 1-6 carbon atoms at a temperature of from −60° to 25° C. for from 0.5 to 3 hours.

The deblocking reaction 7→8 is preferably by hydrolysis. When COOR⁵=silyl ester or mixed anhydride both the imino ether and COOR⁵ are hydrolized; if

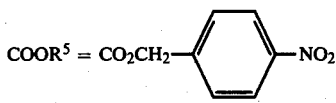

or the like, only imino ether is hydrolized.

Hydrolysis is particularly preferred when the silyl protecting groups are employed. Typically such hydrolysis is conducted in an aqueous solution having a pH of 3 to 5 at a temperature of from 0°-25° C.

Those skilled in the art will recognize that the elements of the above process are known for deacylation of 6- and 7-amido penicillins and caphalosporins. Those skilled in the art will also recognize that there is no criticality as to the identity of the above-described blocking groups or in the precise identity of the side chain at the 2-position of the substrate except, of course, that it bear an acylated amino group. As mentioned above, when the substituents at the 6-position bear functional groups such as the hydroxyl group, protection is desired and is most conveniently accomplished by silylation according to procedures well known in the art. The following examples further illustrate the process of the present invention. All temperatures are given in °C.

EXAMPLE 1

Process for deacylating N-acetyl-6-ethyl-2-[2-aminoethylthio]-1-carbadethiapen-2-em-3-carboxylic acid Anhydrous sodium N-acetyl-6-ethyl-2-[2-aminoethylthio]-1-carbadethiapen-2-em-3-carboxylate (1 mmole) is suspended in anhydrous methylene chloride (5 ml) and the mixture is stirred at room temperature (25° C.) under a nitrogen atmosphere. N,N-dimethylaniline (4 mmole) and dimethyldichlorosilane (0.8 mmole) are added. After stirring 30 minutes at room temperature, the mixture is cooled to −40° C. and treated with phosphorous pentachloride (1.05 mmole). The mixture is stirred an additional 2 hours at −40° C., then cooled to −60° and treated dropwise with n-butanol (20 mmole). After stirring 2 more hours at −40° C., the reaction mixture is added to ice-cold pH 4.5 phosphate buffer (5 ml) and the biphasic mixture is vigorously stirred for 15 mins at 0°-5° C. The aqueous phase is separated, brought to pH 8 with dilute aqueous sodium hydroxide, washed thoroughly with cold ethyl acetate, and concentrated under vaccum to ca. 2 ml. This solution is charged onto a Dowex 50-X4 column (sodium form) which is eluted with water. The appropriate fractions (UV detection) are combined, concentrated under vacuum, and lyophilized to provide 6-ethyl-2-(2-aminoethylthio)-1-carbadethiapen-2-em-3-carboxylic acid.

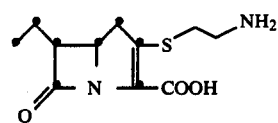

Similar results are obtained when other carboxyl protecting groups are employed. Thus, for example, instead of employing the silylating agent Me₂Cl₂Si, equivalent results are obtained when Me₃SiCl, or AcCl are employed.

EXAMPLE 2

Process for deacylating N-acetyl-6-(1-hydroxyethyl)-2-(2-aminoethylthio)-1-carbadethiapen-2-em-3-carboxylic acid Hexamethyldisilazane (2.0 ml) and trimethylchlorosilane (0.6 ml) are added to a suspension of sodium N-acetyl-6-(1-hydroxyethyl)-2-(2-aminoethylthio)-1-carbadethiapen-2-em-3-carboxylate (0.6 mmole) in anhydrous tetrahydrofuran (15 ml). The resulting mixture is stirred under a nitrogen atmosphere at room temperature for 20 mins and then evaporated under vacuum. The residue is diluted with anhydrous methylene chloride (3 ml), cooled to −40° C., and treated with N,N-dimethylaniline (3 mmole) and phosphorous pentachloride (0.6 mmole). After stirring for 2 hours at −40°, the mixture is cooled to −60° C. and treated dropwise with n-butanol (15 mmole). The mixture is stirred an additional 2 hours at −40° and then added to ice-cold pH 4.5 phosphate buffer (5 ml). The resulting biphasic mixture is stirred vigorously for 15 minutes at 0°-5°. The aqueous phase is separated and processed as described in Example 1 to afford 6-(1-hydroxyethyl)-2-(2-aminoethylthio)-1-carbadethiapen-2-em-3-carboxylic acid.

What is claimed is:

1. A process for preparing

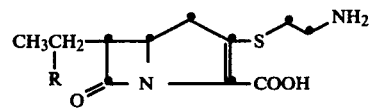

wherein R is hydrogen or hydroxyl, which comprises chlorinating, in the presence of base with a chlorinating agent selected from PCl₅, SOCl₂, or POCl₃ at a temperature of from −50° to 65° C., the silylated compound

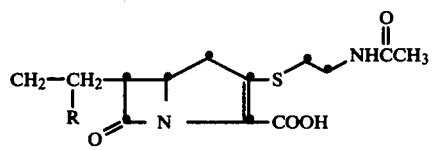

in which the 3-carboxyl group and the hydroxyl group, when R is hydroxyl, are blocked by previous reaction with dimethyldichlorosilane, trimethyl chlorosilane, or hexamethyldisilazane; followed by treating the resulting imino chloride intermediate with an excess of alcohol to yield the corresponding imino ether;

followed by hydrolyzing in aqueous solution at a pH of 3 to 5 at a temperature of from 0°-25° C.; and recovering the desired product thereby produced.

* * * * *